US00PP13677P39

(12) United States Plant Patent
Glenn

(10) Patent No.: US PP13,677 P3
(45) Date of Patent: Mar. 25, 2003

(54) WILLOW OAK TREE NAMED 'QPSTA'

(75) Inventor: Michael M. Glenn, Bogart, GA (US)

(73) Assignee: Tree Introductions, Inc., Bishop, GA (US)

( * ) Notice: Subject to any disclaimer, the term of this patent is extended or adjusted under 35 U.S.C. 154(b) by 0 days.

(21) Appl. No.: 09/834,740

(22) Filed: Apr. 13, 2001

(65) Prior Publication Data

US 2002/0152525 P1 Oct. 17, 2002

(51) Int. Cl.[7] ..... A01H 5/00

(52) U.S. Cl. ..... Plt./225

(58) Field of Search ..... Plt./225

*Primary Examiner*—Bruce R. Campell
*Assistant Examiner*—Susan B. McCormick
(74) *Attorney, Agent, or Firm*—Klarquist Sparkman LLP

(57) ABSTRACT

A Willow Oak tree named 'QPSTA' having dense, narrow-pyramidal branching habit, dense canopy, dominant central leader, and relatively fast growth rate and which is also capable of being reproduced reliably using softwood cutting.

6 Drawing Sheets

LATIN NAME OF THE GENUS AND SPECIES OF THE PLANT CLAIMED

*Quercus phellos.*

VARIETY DENOMINATION

'QPSTA'.

BACKGROUND OF THE INVENTION

The present invention relates to a new and distinct variety of *Quercus phellos,* Willow Oak, which has been given the varietal name 'QPSTA.'

The original tree of this new Willow Oak variety was discovered in 1994 as a chance seedling growing in a cultivated area of a nursery in Oconee County, Ga. It had been purchased as a 12 to 18 inch liner in the spring of 1989 and at that time was planted in a liner field. This tree was transplanted to another field in the spring of 1992 where it was subsequently discovered. In the spring of 1998 this tree was transplanted to an observation area where it has remained since that time. It is now about 12 years old from a seed. The description of this new Willow Oak variety is based on observations of this original tree and of asexually propagated progeny, produced from softwood cuttings, which are about five years old and which are being grown at a nursery in Oconee County, Ga.

Common Willow Oak trees are typically large deciduous trees with a dense crown having an oblong-oval to rounded shape at maturity, generally reaching about 40 to 60 feet high and about 30 to 40 feet wide at maturity, though the largest trees may reach 100 feet in height with an equal spread. Willow Oaks are native to floodplains and adjacent slopes, bottomlands, and rich uplands in a geographic range beginning on the Eastern seaboard from New York to Florida, stretching west to Missouri, Oklahoma and Texas. Willow Oaks grow best in moist, well-drained soils, but adapt well to harsh environmental conditions, and are therefore one of the best oaks for the heat, drought, and humidity of the Southeast, while still readily adaptable to the more arid Midwest. Willow Oak species are typically hardy in USDA Zones 5–9, performs best in zones 6–8, and can survive temperatures as low as −25 degrees Fahrenheit (e.g., in Cincinnati, Ohio). Insofar as I am aware, Willow Oak trees which are commercially available are grown from seedling material, creating a high degree of variability in the industry, both in landscape situations and nurseries. Seedling Willow Oak trees are variable in growth rate and habit, typically lack a central leader, and tend to be open in youth.

This new Willow Oak variety is distinguished from other Willow Oaks known to the inventor by the following unique combination of characteristics: dense, narrow-pyramidal branching habit; dense canopy; dominant central leader; and relatively fast growth rate. When discovered in 1994, the original tree of this new variety was approximately 25% larger than other Willow Oak trees planted at the same time in the same group of seedlings.

BRIEF SUMMARY OF THE INVENTION

In 1996, the original tree of this new Willow Oak variety was successfully propagated by softwood cuttings at my direction. This asexual reproduction was accomplished in Bulloch County, Ga. The progeny have demonstrated that the novel characteristics of this new variety are fixed, stable, and reproduce true to type through asexual propagation. These observations confirm that 'QPSTA' represents a new, distinct, and improved variety of Willow Oak as particularly evidenced by the combination of characteristics described above (dense, narrow-pyramidal branching habit, dense canopy, dominant central leader, and relatively fast growth rate), and which can be asexually propagated reliably using vegetative propagation techniques. Additionally, the progeny, as of this time and growing in Oconee County Ga. have exhibited an annual caliper growth rate of about 1.25 inches per year, compared to an average common Willow Oak seedling growth rate of only about 1 inch per year.

This new variety is particularly suited for use as a street tree and for filling large, open areas such as golf courses, commercial sites, and parks. This new Willow Oak variety provides a uniform, structurally sound tree, and its rapid growth rate will benefit growers who will profit from a faster growing variety of Willow Oak.

BRIEF DESCRIPTION OF THE DRAWINGS

The accompanying photographs illustrate this new Willow Oak variety with color as true as reasonable possible in this type of color photograph.

DETAILED BOTANICAL DESCRIPTION

This invention has not been observed under all possible environmental conditions. The phenotype may vary with variations in growing environment such as temperature, light intensity and day length, rainfall, or nutrient availability, without, however, any variations in genotype. 'QPSTA' Willow Oak trees are currently growing at a nursery in Oconee County, Ga. This particular area of Oconee County has a clay loam soil type, is located in USDA Hardiness Zone 7 and receives average yearly rainfall of 50 inches (typically ranging between 30 and 60 inches for any given year).

The following is a detailed description of the 'QPSTA' Willow Oak variety with color terminology in accordance with The Royal Horticultural Society (R.H.S.) color chart published by The Royal Horticultural Society of London, England. This description is based on observations of the original tree and about five year old progeny.

Parentage: Discovered as a chance seedling of unknown origin growing in a cultivated area of a nursery in Oconee County, Ga.

Figure 1:
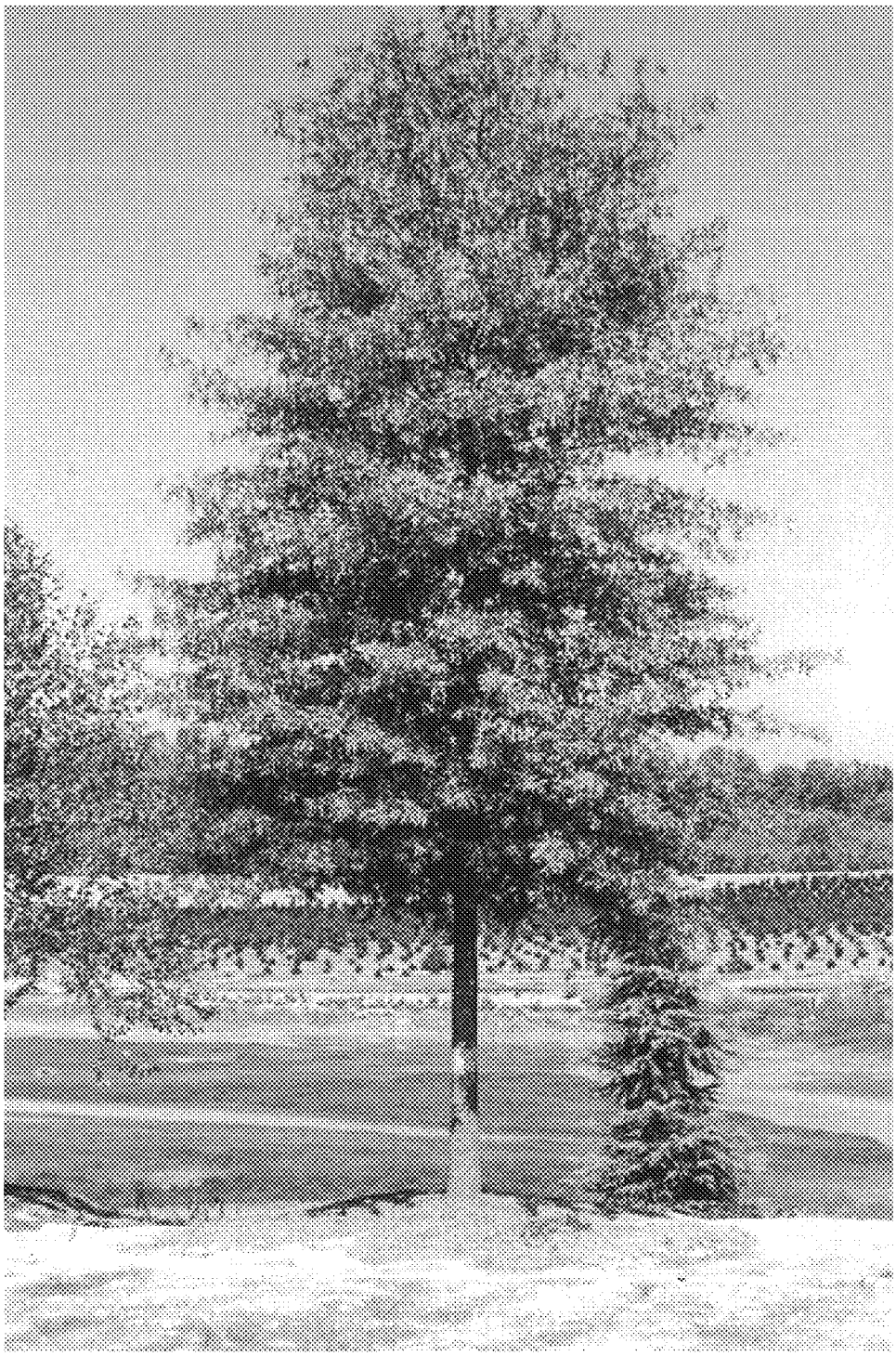
FIG. 1 is a photograph of the original tree of the new variety in summer leaf.
Figure 2:
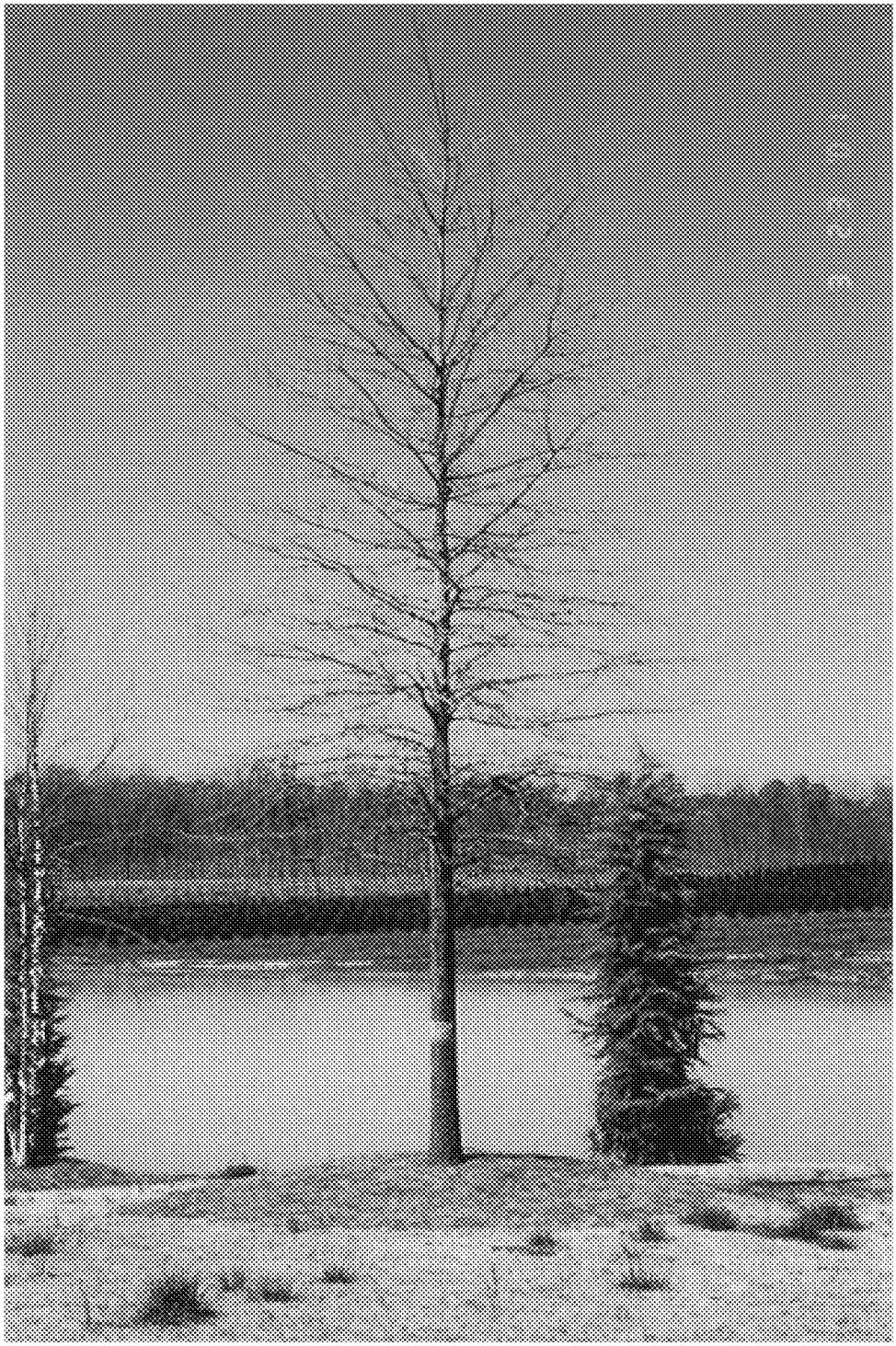
FIG. 2 is a photograph of the original tree of the new variety during winter.

Tree shape: Dense, narrow-pyramidal branching habit, dense canopy, and maintains a dominant central leader (See FIGS. 1 and 2).

Size and growth rate: The original tree, aged 12 years, is currently 9¾ inches in caliper at 12 inches above the ground, about 29 feet high, and about 18 feet wide, thus providing an overall height to width ration of about 1.61. Prior to transplanting to the observation site, the original tree had an average growth in caliper of about 1.25 inches per year. The progeny have also displayed this rapid growth rate characteristic. Root development from time of sticking is approximately four to eight weeks.

Figure 5:
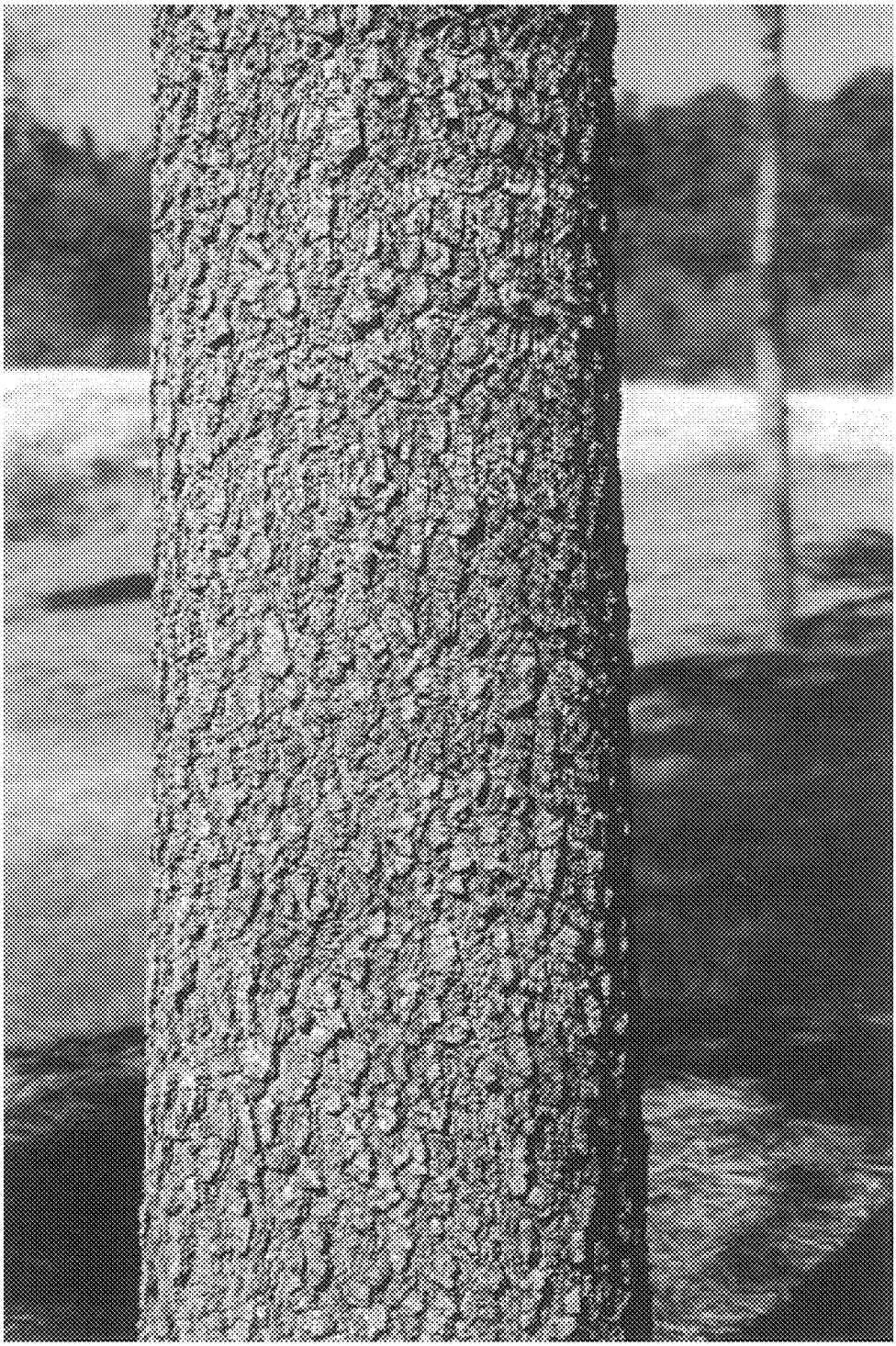
FIG. 5 is a close up of the trunk of the original tree of the new variety.
Figure 6:
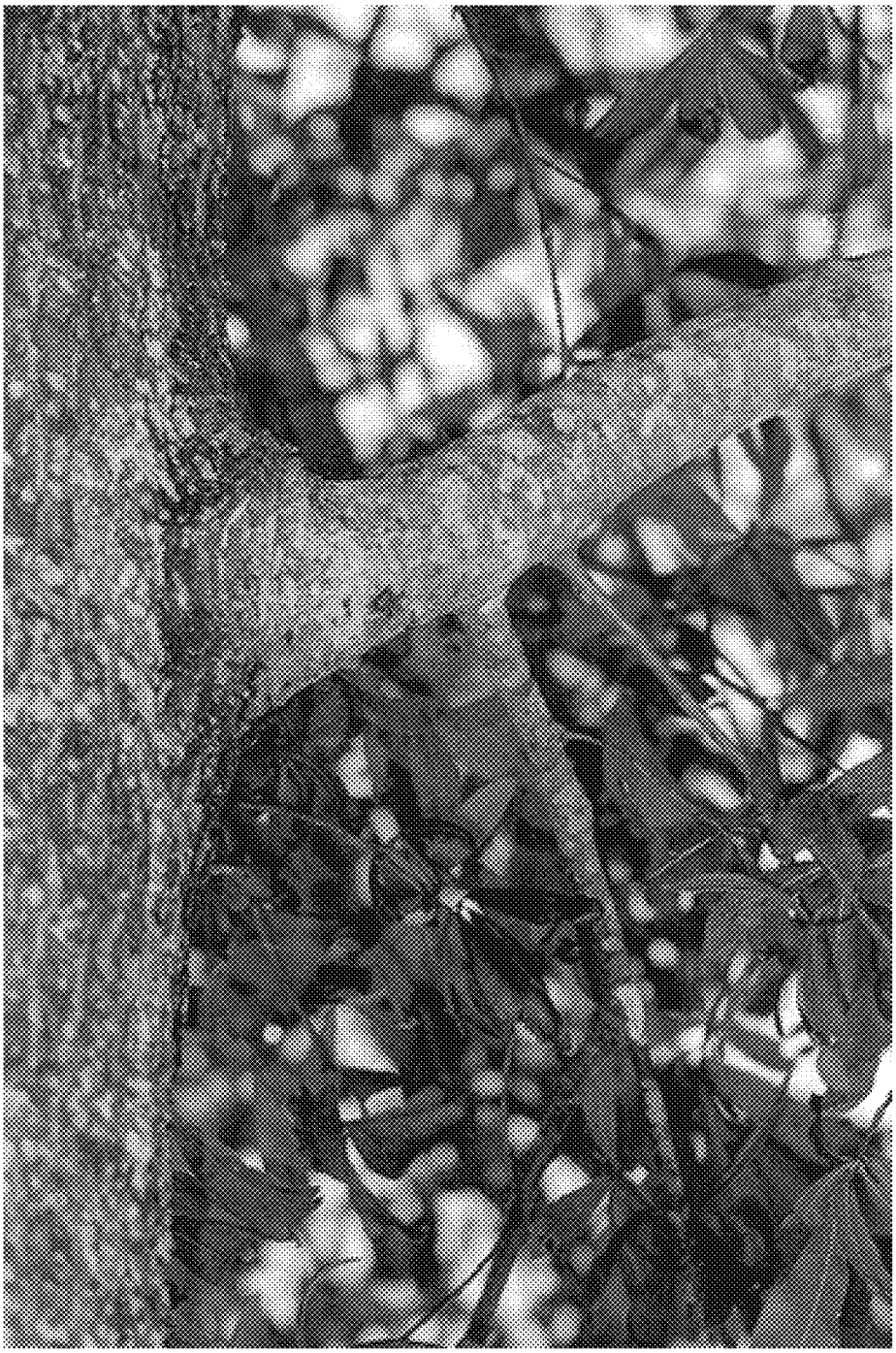
FIG. 6 is a close up of a typical branch of the new variety.

Trunk: Bark is typical of the species, being smooth and gray (RHS 195D) on young trees, and gray (RHS 195D) and, with age, becoming roughened by irregular furrows and thick, more or less scaly ridges (see FIG. 5). Mature bark is grayed green (RHS 194B) in color, also typical of the species.

Branching habit: Denser than typical for the species (see FIG. 1). Primary branches toward the top of the tree emerge at about a 50 degree angle to the leader and branch angle relative to the trunk tends to increase with age (see branches at lower portion of tree in FIG. 2).

Branches: One year old (new growth) branches approximately ¼ inch in diameter with a smooth texture and gray-green (RHS 195B) in color.

Figure 3:
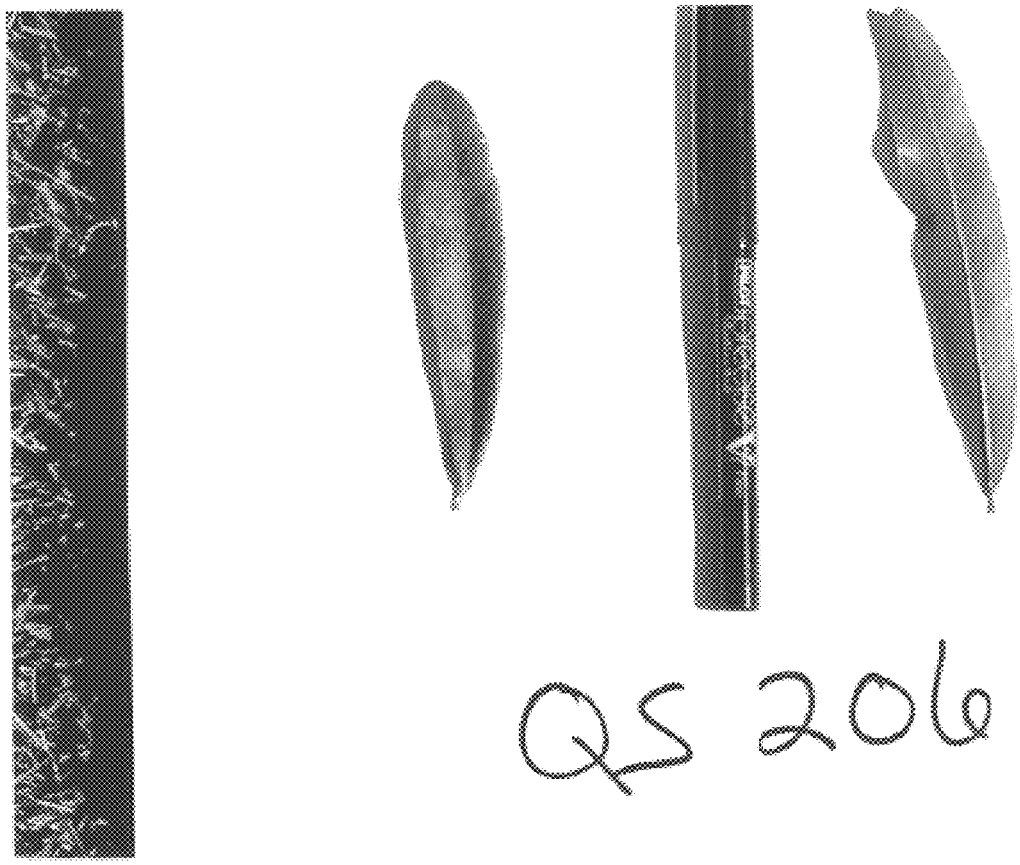
FIG. 3 is a close up of two single leaves from a tree of the new variety, identified as "QS 206" by the nursery's internal identification system. The pen in the picture provides a sizing reference.
Figure 4:
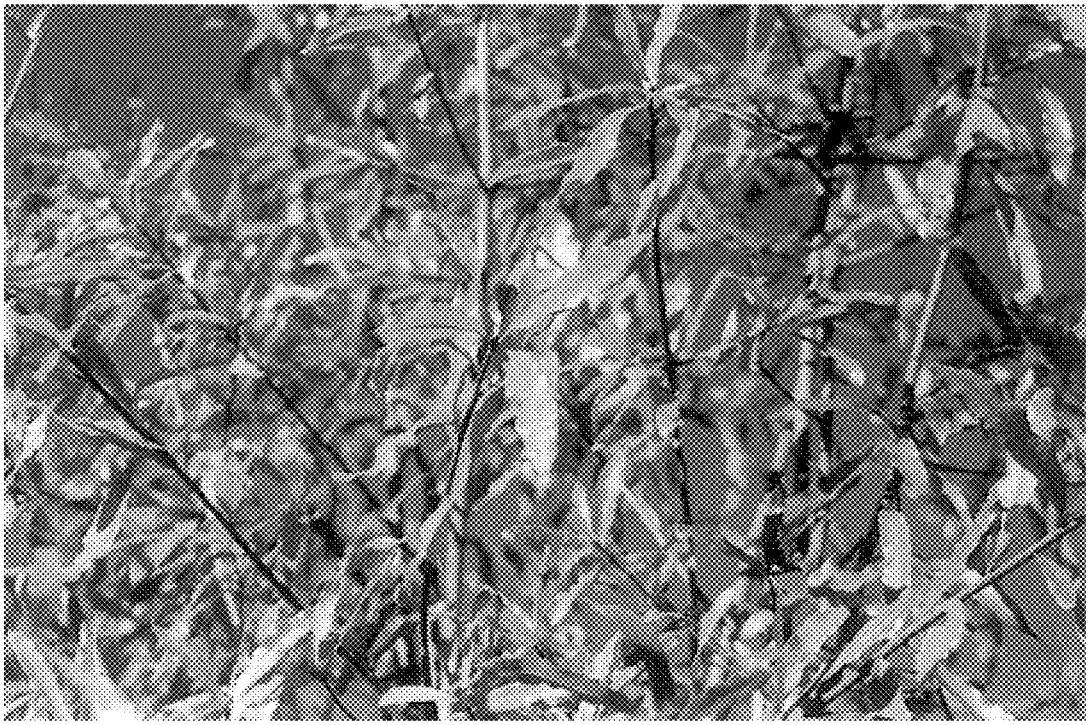
FIG. 4 is a close up of a leaf showing typical fall leaf color of the new variety.

Foliage: Typical of the species. Leaves are alternate, simple; narrowly elliptical or lance-shaped; about 2 to 5½ inches long and one-third to 1 inch wide; acute, slightly wavy, and entire on margins, usually tipped with a bristle. Both the leaf apex and base are acute in shape. Leaves exhibit a pinnate venation pattern with light-green (RHS 146D) veins. Leaves emerge light green (RHS 144B) in spring, becoming dark green (RHS 137A) in summer. On mature leaves, the upper leaf surface is dark green (RHS 137A), and the lower leaf surface is a lighter green (RHS 146B). Fall color is usually yellow-brown (RHS 13A). See FIGS. 3 and 4. Petiole is approximately ¼ to ⅜ inch long, approximately 1/16 inch in diameter, and light green (RHS 146D) in color.

Buds: Typical of the species. Imbricate, one-eighth to one-quarter inch long, ovoid, sharp-pointed, and chestnut brown (RHS 200D) in color.

Flowers: Typical of the species. Willow Oaks, including the new variety, are monoecious. Staminate catkins are pendent and clustered. Individual flowers are typically a 4- to 7-lobed calyx enclosing about 6 or more stamens. Pistillate flowers are solitary or borne in spikes from axils of new leaves. Individual flowers commonly consist of a 6-lobed calyx surrounding an ovary, the whole being partly enclosed in an involucre. Date of initial bloom (in Oconee County, Ga.) is approximately April 1, with a duration of approximately 10–14 days.

Fruit: Typical of the species. The acorn, to date observed in the original tree only, is solitary or paired, about ½ inch or less long and about ½ inch or less wide, subglobose, and is enclosed at the base by a thin saucer like cap. The acorn itself has alternating brown (RHS 177A) and black (RHS 200A) bands.

Root system: Typical of the species. Oaks typically have coarse root systems, but Willow Oak trees, including the new variety, have a more fibrous root system than the genus.

Disease and pest resistance: Appears to be typical of the species, but may be somewhat more resistant to spider mites.

Winter hardiness: Not yet determined, hardy at least in zone 7 where it has been grown and observed.

I claim:

1. A new and distinct variety of Willow Oak tree named 'QPSTA,' substantially as herein illustrated and described, characterized particularly as to novelty by its unique dense, narrow-pyramidal branching habit, dense canopy, dominant central leader, and relatively fast growth rate.

* * * * *